United States Patent [19]

Krämer

[11] Patent Number: 5,439,036
[45] Date of Patent: Aug. 8, 1995

[54] METHOD AND APPARATUS FOR THE AUTOMATIC CHECKING AND QUALITY DETERMINATION OF TABLETS OR PILLS

[76] Inventor: Norbert Krämer, Röntgenstrasse 68, 64291 Darmstadt, Germany

[21] Appl. No.: 219,115

[22] Filed: Mar. 29, 1994

[30] Foreign Application Priority Data

Mar. 29, 1993 [DE] Germany .......................... 43 09 978.5

[51] Int. Cl.[6] .......................... B65B 1/04; B65B 3/04
[52] U.S. Cl. .......................................... 141/1; 141/83; 141/94; 141/196; 177/60
[58] Field of Search ................. 141/1, 83, 94, 98, 234, 141/237, 244, 192, 196, 198; 177/60, 50; 221/163, 15

[56] References Cited

U.S. PATENT DOCUMENTS

| | | | |
|---|---|---|---|
| 3,785,525 | 1/1974 | Handeland | 221/15 |
| 4,537,229 | 8/1985 | Sashiki et al. | 141/83 |
| 5,022,444 | 6/1991 | Kendall et al. | 141/83 |
| 5,127,450 | 7/1992 | Saatkamp | 141/9 |

FOREIGN PATENT DOCUMENTS 3628757 3/1988 Germany .
4118878 1/1993 Germany .

*Primary Examiner*—J. Casimer Jacyna
*Assistant Examiner*—Steven O. Douglas
*Attorney, Agent, or Firm*—Horst M. Kasper

[57] ABSTRACT

A method and an apparatus is provided for the automatic testing of tablets or pills, discharging from a tablet machine (20). The tablets are delivered to containers (5, 6). Tablet batch samplings are removed from the tablet stream for performing a quality control function. The tablet batch samplings are tested and checked in a tablet checking device (15) according to preset quality characteristics. The containers (5, 6) are disposed on a scale (2, 3). The weight of the container including the contents of tablets is continuously measured. The weight is converted into an electrical signal, which is input into a computing and control unit (19) within the tablet checking device (15). An identification occurs for each container (5, 6). The identification is also input into the computing and control unit (19). Batch samplings are removed at preset intervals from the tablet stream discharging into the to be filled container (5, 6). The batch samplings are fed to the tablet checking device (15). The test results are stored in the computing and control unit (19) under allocation to the corresponding container (5, 6). The test results are possibly printed out onto a print substrate carrier forming a protocol for the corresponding container.

20 Claims, 1 Drawing Sheet

METHOD AND APPARATUS FOR THE AUTOMATIC CHECKING AND QUALITY DETERMINATION OF TABLETS OR PILLS

BACKGROUND OF THE INVENTION

1. Field of the Invention

The invention relates to a method for an automatic checking and quality determination of tablets or pills, where the tablets or pills are fed continuously from a tablet machine or pill pressing machine, as well as an apparatus for the automatic checking and quality control of tablets or pills.

2. Brief Description of the Background of the Invention Including Prior Art

Tablets, delivered from the tablet-pressing machine, are conventionally filled into drums in the tablet and pill production, where one charge for the drums represents one batch. Samples are taken at fixed and/or defined intervals from the tablet stream delivered by the tablet machine. These batch samplings are fed to a device for automatic quality control. The samples are subjected to various tests in this device such as, among others, a hardness test, a thickness measurement, a diameter determination, weighing, calibration. The results of these tests are compiled into reports and/or protocols. The batch samplings are removed from the tablet stream during the normal filling operation of the drums. The drums are automatically filled and thus the tablet stream can be directed from a full drum to an empty drum. Such modes of operations are known, among others, from the German Patent document DE 4,118,878-A1.

Since the withdrawal of the batch sampling occurs independently of the filling operation of the drums, and since the drums are continued to be filled during the removal of the batch samples, it has not been possible up to now to associate the protocols, prepared by the test device, with a specific drum. Until today it has only been possible to associate the protocols to an entire charge. Thus, if freak stray values are discovered within the protocols, which are not acceptable based on the preset quality specifications, then the entire charge has to be rejected, which can be associated with substantial expenditures.

A method for the quality assurance in the production of tablets has become known from the German Patent document DE-3,628,757-A1. According to this method, samples are withdrawn during the production of the tablets, where these samples are comprised of a plurality of tablets. The combined actual value of the weight of said plurality of tablets is compared to the set value of the weight. The tablet-compressing machine is then readjusted corresponding to the deviation between the actual value and the set value in order to bring the tablet weight to the set value. The weight of the individual tablets of the sampling are measured and compared with each other before a readjustment of the tablet machine. Upon determination that one or more tablets of the samplings deviate substantially in their weight from the set value, the statistics are rectified through a correcting calculation and the corrected value is employed for readjustment. The statistical evaluation of the measurement results as well as an automatic correcting calculation or a request for a second batch sampling occurs as determined with the aid of a computer. The data output of the computer is connected to a device for the readjustment of the filling charge weight or amount. This process is employed during the production of the tablets and does therefore not allow an association of the measurement results to a specific drum since, as stated above, the removal of a batch sampling occurs independent of the filling operation of the drums.

SUMMARY OF THE INVENTION

1. Purposes of the Invention

It is an object of the present invention to provide for a method and a device for the automatic checking and quality control of tablets or pills, where the tablets or pills are fed continuously from a tablet machine or pill pressing machine, and where an association of sample tablets, removed from a tablet stream, is possible to a specific drum which is in the process of being filled by the tablet machine.

It is another object of the present invention to improve the monitoring of the properties of samples taken from a product flow derived from a tablet machine.

These and other objects and advantages of the present invention will become evident from the description which follows.

2. Brief Description of the Invention

The present invention provides for a method for automatic checking and quality control of tablets or pills. A plurality of containers is disposed on a scale. Tablets or pills are delivered quasi continuously from a tablet machine or pill machine to a plurality of containers. The weight of the momentarily being filled container including the contents of tablets or pills is continuously monitored. Said weight is converted into a corresponding electrical signal. Said electrical signal is entered continuously into a computing and control unit within a tablet checking device or a pill checking device. An identification of each container of the plurality of containers is performed. The resulting identification is entered into the computing and control unit. Tablet batch samplings or pill batch samplings are withdrawn at preset intervals from a tablet stream or pill stream discharging into the container presently being filled for performing an automatic quality control. The tablet batch samplings or pill batch samplings are fed to the tablet checking device or pill checking device. The tablet batch samplings or pill batch samplings are tested and checked in the tablet checking device or the pill checking device according to preset quality characteristics. Test results thereby obtained are stored in the computing and control unit under association of the test results with the container presently to be filled. A recording of the test results onto a recording substrate carrier is performed to render them readable and thereby forming a protocol for the corresponding container.

Steps based on a weight change of the presently being filled container can be employed to time a withdrawal of the batch samplings at the preset intervals according to an increasing weight of the container during filling.

The steps of withdrawal can be timed to be steps of weight changes of n-kilograms of the container being presently filled, such that the withdrawal of one batch sampling occurs after a weight increase of n-kilograms.

Steps based on an elapsed time period of the presently being filled container can be employed to time a withdrawal of the batch samplings at the preset intervals according to an increasing time period of a filling process of the container.

The steps of withdrawal can be timed to be steps of time periods of n-minutes, such that the withdrawal of one batch sampling occurs every n-minutes.

Preferably, the protocols for all batch samplings are compiled for a specific container and the protocols are printed out for all batch samplings for a specific container at the end of a filling operation.

Preferably, there is a continuous request for an actual weight of the containers, a container number for identification, and a container substitution for identification, as well as the batch samplings by the computing and control unit of the tablet checking device or pill checking device.

The solution of the object of the present invention is provided by a method for the automatic checking and quality control of tablets or pills, continuously discharged from a tablet machine or pill-pressing machine. The tablets or pills are discharged into a plurality of containers. Tablet samples or pill samples provided in batch are removed from the tablet stream or pill stream for performing an automatic quality control. The tablet samples or pill samples are checked in a tablet testing device or pill testing device according to specified and predetermined quality characteristics. According to the present invention, each container is placed on a scale. The weight of the momentarily being filled container, including the contents of tablets or pills, is continuously measured. Said weight is converted into a corresponding electrical signal and this signal is continuously input into a computing and control unit within the tablet checking device or pill checking device. An identification is performed for each container which is also input into the computing and control unit. Tablet samples and pill samples are removed at preset intervals from the tablet stream or pill stream leading to the momentarily to be filled container and these removed tablet samples and pill samples are fed to the tablet checking device or pill checking device and are checked according to preset quality values stored in the tablet checking device or pill checking device. The test results are stored in the computing and control unit with reference to the momentarily to be filled container and are possibly printed visually visible onto a printing carrier as a protocol for the corresponding container.

An apparatus is provided for performing the invention method for automatic testing and checking and for determining quality of tablets or pills discharging continuously from a tablet machine or pill machine. A plurality of containers is provided. Tablets or pills are delivered into the plurality of containers. A scale is connected to an electronic interface. In each case a container of the plurality of containers is disposed on the scale, wherein the scale is capable of continuously measuring an instant weight of the container being filled and including contents of tablets or pills. The scale generates and emits a corresponding electrical signal through the electronic interface. An identification device of the container delivers an identification signal. Tablet batch samplings or pill batch samplings are tested and checked in a tablet testing and checking device or pill testing and checking device according to preset quality characteristics. The actual electrical signal of the scale as well as the identification signal of the respective container are input through the electronic interface to the tablet testing and checking device or pill testing and checking device. An electronic computing and control unit is connected to the tablet testing and checking device or pill testing and checking device. The tablet batch samplings or pill batch samplings are withdrawn at preset intervals from a tablet stream or pill stream discharging into the container presently to be filled for performing an automatic quality control. Said tablet batch samplings or pill batch samplings are fed to the tablet testing and checking device or pill testing and checking device and are tested and checked. A storage and display unit is connected to the tablet testing and checking device or pill testing and checking device for storing and discharging test results in their association with the container presently being filled. The test results of all batch samplings for the container presently being filled are combined.

The electronic computing and control unit can preset intervals for removal of the batch samplings in steps according to an increasing weight of the container during filling in a weight-controlled manner.

Preferably, the preset intervals are provided in steps of n-kilograms of weight change of the container being filled.

The electronic computing and control unit can preset intervals for removal of the batch samplings in steps according to elapsed time periods during filling the container based on a time-control.

Preferably, the preset intervals are provided in steps of n-minutes of elapsed time during the filling of the container.

The invention method offers the outstanding advantage that this method allows to remove batch samplings from the tablet stream by controlling either the weight or time period, and batch samplings can be fed to the testing and monitoring device, and the resulting protocols can subsequently be unequivocally associated with the respective container just filled.

For purposes of explanation, it is assumed that the tablet weight of a fully filled container amounts to 18 kilograms. The changing weight of the container starting from an empty state ending in a full state is continuously input as electrical signal through an interface of the scale to the tablet checking device or pill checking device. The continuous removal of batch samplings occurs at preset intervals, for example, based on using weight changes as control input, for example in 1-kilogram steps, such that 18 batch samplings are performed per container in case of a final weight of 18 kilograms per filled container. The protocols and test results for these batch samplings can be printed out together, for example on a self-adhesive label, where the label can be attached to the corresponding container.

In the same way, the preset intervals can be time-controlled only, for example, such that a batch sampling is removed every 10 minutes. In this manner, 15 batch samplings can be removed and tested in case of a filling time of, for example, 150 minutes per container. It is essential in this case that an identification or, respectively, a marking of the respective container occurs, while the container is on the scale at that moment and is being filled.

In an advantageous manner, the request and initialization of the batch samplings occurs from the tablet checking device or pill checking device, where the tablet checking device or pill checking device automatically removes the batch samplings from the tablet stream being filled into a specific container. In addition, the testing and checking system requests the actual weight of the container, the container number, and also the container substitution, where the container substitution can be performed either manually or automatically.

The present invention provides a method and a device for the first time in an advantageous manner, and allowing communicating between a scale having electronic interface and a checking and testing system in such a way that the prepared protocols and test results based on testing criteria and testing standards can be allocated directly to the corresponding container for a plurality of batch samplings, where the container is being filled or, respectively, was just filled during the time of a removal of the respective batch samplings.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which is shown a possible embodiment of the present invention.

DESCRIPTION OF INVENTION AND PREFERRED EMBODIMENT

Figure 1:
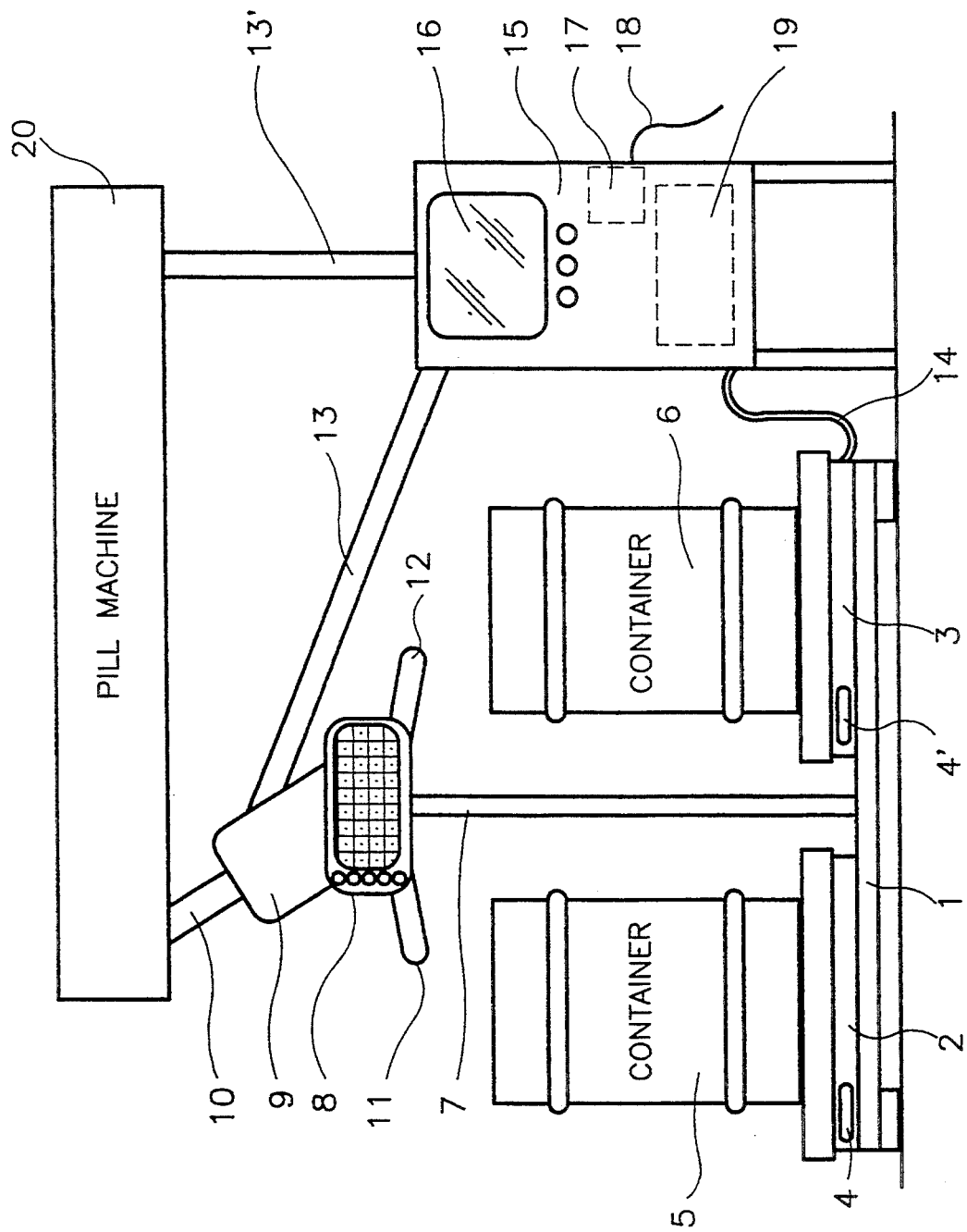
FIG. 1 is a view of a schematic diagram illustrating the automatic testing apparatus.

A method is provided for automatic checking and quality control of tablets or pills, delivered quasi continuously from a tablet machine or pill machine 20. The tablets or pills are delivered to a plurality of containers 5, 6. Tablet batch samplings or pill batch samplings are removed from a tablet stream or pill stream for performing an automatic quality control. The tablet batch samplings or pill batch samplings are tested and checked in a tablet checking device or a pill checking device 15 according to preset quality characteristics. Containers 5, 6 are in each case disposed on a scale 2, 3. A weight of the momentarily being filled container including the contents of tablets or pills is continuously measured, wherein said weight is converted into a corresponding electrical signal. Said electrical signal is continuously input into a computing and control unit 19 within the tablet checking device or the pill checking device 15. An identification occurs for each container 5, 6, wherein the identification is also input into the computing and control unit 19. The tablet batch samplings or pill batch samplings are removed at preset intervals from the tablet stream or pill stream discharging into the momentarily to be filled container 5, 6. The tablet batch samplings or pill batch samplings are fed to the tablet checking device or pill checking device 15. The tablet batch samplings or pill batch samplings are checked and tested in the tablet checking device or pill checking device 15 according to preset quality characteristics. Test results are stored in the computing and control unit 19 under association with the container 5, 6 presently to be filled. The test results are possibly printed out visually visible onto a print substrate carrier 18 forming a protocol for the corresponding container.

The removal of the batch samplings at the preset intervals can occur weight-controlled in steps according to an increasing weight of the container 5, 6 during filling, for example in steps of n-kilograms, such that the removal of one batch sampling occurs for a weight increase of n-kilograms.

The removal of the batch samplings can occur time-controlled based on elapsed time periods, for example in steps of n-minutes, such that the removal of one batch sampling occurs every n-minutes.

The protocols for all batch samplings for a specific container can be compiled and printed out at the end of a filling operation.

Preferably, the computing and control unit 19 of the tablet checking device or pill checking device 15 continuously requests an actual weight of the containers 5, 6, a container number for identification and a container substitution for identification, as well as the batch samplings.

An apparatus is provided for automatic testing and checking and for determining quality of tablets or pills discharging continuously from a tablet machine or pill machine 20, and for delivering said tablets or pills into a plurality of containers 5, 6. Tablet batch samplings or pill batch samplings are withdrawable from a tablet stream or pill stream for performing an automatic quality control, wherein the tablet batch samplings or pill batch samplings are tested and checked in a tablet testing and checking device or pill testing and checking device 15 according to preset quality characteristics. A scale 2, 3 exhibits an electronic interface. In each case a container 5, 6 is disposed on the scale 2, 3. The scale 2, 3 is capable of continuously measuring the instant weight of the container being filled and including the contents of tablets or pills. The scale 2, 3 generates and emits a corresponding electrical signal. There is included an identification device of the container 5, 6. An electronic computing and control unit 19 is coordinated to the tablet testing and checking device or pill testing and checking device 15. The actual electrical signal of the scale 2, 3 as well as the identification of the respective container 5, 6 are input through the electronic interface to the tablet testing and checking device or pill testing and checking device 15. Tablet batch samplings or pill batch samplings are removed at preset intervals from the tablet stream or pill stream discharging into the container presently to be filled. Said tablet batch samplings or pill batch samplings are fed to the tablet testing and checking device or pill testing and checking device 15 and are tested and checked. A storage and display unit 16, 17 is disposed in the tablet testing and checking device or pill testing and checking device 15 for storing and discharging the test results based on association to the container 5, 6 presently being filled. The test results of all batch samplings for one container are combined.

Preferably, the preset intervals for the removal of the batch samplings occur in steps according to the increasing weight of the container 5, 6 during the filling in a weight-controlled manner or in time intervals only based on a time-control, for example in steps of n-kilograms and in steps of n-minutes, respectively.

The storage and display unit can be formed by a display device 16 and by a protocol printer 17.

At least one scale is disposed on a support 1. In FIG. 1 there are shown two scales 2, 3. Each scale 2, 3 exhibits an electronic pressure gauge or load cell 4, 4' and an electronic interface. In each case, a container 5, 6 can be placed on the scale. At the same time, the support plate 1 can be placed under a support column 7. An operator control panel 8 with a data-entry keyboard is disposed at the support column 7.

A separator switch 9 is connected to two outlet pipes 11, 12. The outlet pipes 11, 12 are in each case coordinated to one of the containers 5, 6 on the respective scales 2, 3. A feed line 10 leads into the separator switch 9. The feed line 10 connects to a tablet machine 20 for pressing materials into tablets, not illustrated. Furthermore, the separator switch 9 can be connected to a third outlet pipe 13 leading to a tablet testing and checking device 15. The tablet testing and checking device can be substituted by a pill testing and checking device and any dispensing entity testing and checking device can be employed. The tablet testing and checking device 15 exhibits a display device 16 as well as a protocol printer 17. In addition, the tablet testing and checking device 15 can include a direct feed line 13' connecting to the tablet machine 20. The scales 2, 3 or, respectively, the load cells 4, 4' are connected with the interfaces and an electrical feed line 14 to the tablet testing and checking device 15.

The tablet machine 20 quasi-continuously produces tablets. These tablets are fed through the feed line 10 to the separator switch 9. It is assumed that the container 6 is being filled at this moment. After placing the container 6 onto the scale, the container 6 is identified by the tablet testing and checking device 15 through the interface of the scale 3. The simplest identification represents a consecutive numbering of the containers which are sequentially filled. Only the exact sequential placement of the containers 5, 6 onto the scales 2, 3 and the removal of the filled containers in sequence from the scales 2, 3 has to occur for the identification of the individual containers. At the start of the filling operation, the tare weight of the container is entered into the tablet testing and checking device. In addition, the removal of batch samplings with the tablet testing and checking device is preset such that, for example, a batch sampling is removed during the filling operation per each n kilogram of filling weight. For this purpose, the actual weight of the container 6 is input in the tablet testing and checking device 15. The tablet testing and checking device 15 requests in each case a batch sampling either from the separator switch 9 through the outlet pipe 13 or directly from the tablet machine 20 through the direct feed line 13' after each completion of an n kilogram step. If the container contents is for example to amount to 18 kilograms, then, in case of 1-kilogram steps, 18 batch samplings have been removed and tested and checked at the end of the filling operation of the container. All protocols and test results of the batch samplings can now be printed with a printer 17 onto a printing substrate carrier 18. Based on the identification of the respective container, there occurs an unequivocal association of the batch sampling to the respective filled container. For example, the printing carrier 18 can be a self-adhesive label which can be attached to the respective container after the filling operation and the establishment of all protocols. The separator switch 9 can automatically switch to a second empty container 5, where in the meantime the second empty container has been placed in position after the end weight level of the first container 6 has been reached.

If it is determined during the checking of the protocols that the preset quality standards of the tablets or pills have not been met in specific protocols, then only the contents of the respective container has to be separated out and discarded and not the entire charge comprising a plurality of containers.

The object of the present invention shows substantial commercial application and utility in the pharmaceutical industry in the production and processing of tablets or pills since with the invention method or, respectively, the invention system, batch samplings are removed either weight-controlled or time-controlled from the tablet stream and are fed to the tablet testing and checking device. Subsequently, the protocols can be unequivocally and non-confusingly associated with the just filled or, respectively, just being filled container in a useful manner.

Pills are in general small, round solid dosage forms containing a medicinal agent and intended for oral administration. Pills and tablets may be defined as solid pharmaceutical dosage forms, frequently to be administered orally.

It will be understood that each of the elements described above, or two or more together, may also find a useful application in other types of quality control systems and methods differing from the types described above.

While the invention has been illustrated and described as embodied in the context of a method and system for the automatic checking and quality specification of tablets or pills, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method for automatic checking and quality control of tablets or pills comprising
   disposing a plurality of containers on a scale;
   delivering tablets or pills quasi continuously from a tablet machine or pill machine to a plurality of containers;
   monitoring continuously the weight of the momentarily being filled container including contents of tablets or pills;
   converting said weight into a corresponding electrical signal;
   entering continuously said electrical signal into a computing and control unit within a tablet checking device or a pill checking device;
   identifying each container of the plurality of containers;
   entering the resulting identification into the computing and control unit;
   withdrawing at preset intervals tablet batch samplings or pill batch samplings from a tablet stream or pill stream discharging into the container presently being filled for performing an automatic quality control;
   feeding the tablet batch samplings or pill batch samplings to the tablet checking device or pill checking device;
   testing and checking the tablet batch samplings or pill batch samplings in the tablet checking device or the pill checking device according to preset quality characteristics;
   storing thereby obtained test results in the computing and control unit under association of the test results with the container presently to be filled;
   recording the test results onto a recording substrate carrier to render them readable and thereby forming a protocol for the corresponding container.

2. The method according to claim 1, further comprising the step of
employing steps based on a weight change of the presently being filled container to time a withdrawal of the batch samplings at the preset intervals according to an increasing weight of the container during filling.

3. The method according to claim 2, further comprising the step of
timing the steps of withdrawal to be steps of weight changes of n-kilograms of the container being presently filled, such that the withdrawal of one batch sampling occurs after a weight increase of n-kilograms.

4. The method according to claim 1, further comprising the step of
employing steps based on an elapsed time period of the presently being filled container to time a withdrawal of the batch samplings at the preset intervals according to an increasing time period of a filling process of the container.

5. The method according to claim 4, further comprising the step of
timing the steps of withdrawal to be steps of time periods of n-minutes, such that the withdrawal of one batch sampling occurs every n-minutes.

6. The method according to claim 1, further comprising the step of
compiling the protocols for all batch samplings for a specific container and printing out the protocols for all batch samplings for a specific container at the end of a filling operation.

7. The method according to claim 1 further comprising the steps of
continuously requesting an actual weight of the containers, a container number for identification, and a container substitution for identification, as well as the batch samplings by the computing and control unit of the tablet checking device or pill checking device.

8. A method for automatic checking and quality control of tablets or pills, delivered quasi continuously from a tablet machine or pill machine (20), wherein the tablets or pills are delivered to a plurality of containers (5, 6), wherein tablet batch samplings or pill batch samplings are removed from a tablet stream or pill stream for performing an automatic quality control, wherein the tablet batch samplings or pill batch samplings are tested and checked in a tablet checking device or a pill checking device (15) according to preset quality characteristics, wherein
(a) containers (5, 6) are in each case disposed on a scale (2, 3), wherein a weight of the momentarily being filled container including contents of tablets or pills is continuously measured, wherein said weight is converted into a corresponding electrical signal, and wherein said electrical signal is continuously input into a computing and control unit (19) within the tablet checking device or the pill checking device (15),
(b) an identification occurs for each container (5, 6), wherein the identification is also input into the computing and control unit (19),
(c) the tablet batch samplings or pill batch samplings are removed at preset intervals from the tablet stream or pill stream discharging into the momentarily to be filled container (5, 6), wherein the tablet batch samplings or pill batch samplings are fed to the tablet checking device or pill checking device (15), and wherein the tablet batch samplings or pill batch samplings are checked and tested in the tablet checking device or pill checking device (15) according to preset quality characteristics,
(d) test results are stored in the computing and control unit (19) under association with the container (5, 6) presently to be filled, and wherein the test results are possibly printed out visually visible onto a print substrate carrier (18) forming a protocol for the corresponding container.

9. The method according to claim 8, wherein removal of the batch samplings at the preset intervals occurs weight-controlled in steps according to an increasing weight of the container (5, 6) during filling, for example in steps of n-kilograms, such that the removal of one batch sampling occurs for a weight increase of n-kilograms.

10. The method according to claim 9, wherein removal of the batch samplings occurs time-controlled based on elapsed time periods, for example in steps of n-minutes, such that the removal of one batch sampling occurs every n-minutes.

11. The method according to claim 8, wherein the protocols for all batch samplings for a specific container are compiled and printed out at the end of a filling operation.

12. The method according to claim 8, wherein the computing and control unit (19) of the tablet checking device or pill checking device (15) continuously requests an actual weight of the containers (5, 6), a container number for identification and a container substitution for identification, as well as the batch samplings.

13. An apparatus for automatic testing and checking and for determining quality of tablets or pills discharging continuously from a tablet machine or pill machine comprising
a plurality of containers, wherein tablets or pills are delivered into the plurality of containers;
a scale connected to an electronic interface, wherein in each case a container of the plurality of containers is disposed on the scale, wherein the scale is capable of continuously measuring an instant weight of the container being filled and including contents of tablets or pills, and wherein the scale generates and emits a corresponding electrical signal through the electronic interface;
an identification device of the container delivering an identification signal;
a tablet testing and checking device or pill testing and checking device, wherein tablet batch samplings or pill batch samplings are tested and checked in the tablet testing and checking device or pill testing and checking device according to preset quality characteristics, and wherein the actual electrical signal of the scale as well as the identification signal of the respective container are input through the electronic interface to the tablet testing and checking device or pill testing and checking device;
an electronic computing and control unit connected to the tablet testing and checking device or pill testing and checking device, wherein the tablet batch samplings or pill batch samplings are withdrawn at preset intervals from a tablet stream or pill stream discharging into the container presently to be filled for performing an automatic quality control, and wherein said tablet batch samplings or pill batch samplings are fed to the tablet testing and checking device or pill testing and checking device and are tested and checked;

a storage and display unit connected to the tablet testing and checking device or pill testing and checking device for storing and discharging test results in their association with the container presently being filled, and wherein the test results of all batch samplings for the container presently being filled are combined.

14. The apparatus according to claim 13, wherein the electronic computing and control unit presets intervals for removal of the batch samplings in steps according to an increasing weight of the container during filling in a weight-controlled manner.

15. The apparatus according to claim 14, wherein the preset intervals are provided in steps of n-kilograms of weight change of the container being filled.

16. The apparatus according to claim 13, wherein the electronic computing and control unit presets intervals for removal of the batch samplings in steps according to elapsed time periods during filling the container based on a time-control.

17. The apparatus according to claim 16, wherein the preset intervals are provided in steps of n-minutes of elapsed time during the filling of the container.

18. An apparatus for automatic testing and checking and for determining quality of tablets or pills discharging continuously from a tablet machine or pill machine (20), and for delivering said tablets or pills into a plurality of containers (5, 6), wherein tablet batch samplings or pill batch samplings are withdrawable from a tablet stream or pill stream for performing an automatic quality control, wherein the tablet batch samplings or pill batch samplings are tested and checked in a tablet testing and checking device or pill testing and checking device (15) according to preset quality characteristics, comprising (a) a scale (2, 3) exhibiting an electronic interface, wherein in each case a container (5, 6) is disposed on the scale (2, 3), wherein the scale (2, 3) is capable of continuously measuring the instant weight of the container being filled and including the contents of tablets or pills, and wherein the scale (2, 3) generates and emits a corresponding electrical signal, (b) an identification device of the container (5, 6), (c) an electronic computing and control unit (19) coordinated to the tablet testing and checking device or pill testing and checking device (15), wherein the actual electrical signal of the scale (2, 3) as well as the identification of the respective container (5, 6) are input through the electronic interface to the tablet testing and checking device or pill testing and checking device (15), wherein tablet batch samplings or pill batch samplings are removed at preset intervals from the tablet stream or pill stream discharging into the container presently to be filled, and wherein said tablet batch samplings or pill batch samplings are fed to the tablet testing and checking device or pill testing and checking device (15) and are tested and checked, (d) a storage and display unit (16, 17) disposed in the tablet testing and checking device or pill testing and checking device (15) for storing and discharging the test results based on association to the container (5, 6) presently being filled, and wherein the test results of all batch samplings for one container are combined.

19. The apparatus according to claim 18, wherein the preset intervals for the removal of the batch samplings occur in steps according to the increasing weight of the container (5, 6) during the filling in a weight-controlled manner or in time intervals only based on a time-control, for example in steps of n-kilograms and in steps of n-minutes, respectively.

20. The apparatus according to claim 18, wherein the storage and display unit is formed by a display device (16) and by a protocol printer.

* * * * *